(12) United States Patent
Wolters et al.

(10) Patent No.: US 9,255,891 B2
(45) Date of Patent: Feb. 9, 2016

(54) INSPECTION BEAM SHAPING FOR IMPROVED DETECTION SENSITIVITY

(71) Applicant: KLA-Tencor Corporation, Milpitas, CA (US)

(72) Inventors: Christian Wolters, San Jose, CA (US); Zhiwei Xu, Sunnyvale, CA (US); Juergen Reich, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 52 days.

(21) Appl. No.: 14/036,360

(22) Filed: Sep. 25, 2013

(65) Prior Publication Data

US 2014/0139829 A1 May 22, 2014

Related U.S. Application Data

(60) Provisional application No. 61/728,707, filed on Nov. 20, 2012.

(51) Int. Cl.
*G01N 21/00* (2006.01)
*G01N 21/95* (2006.01)

(52) U.S. Cl.
CPC .................... *G01N 21/9501* (2013.01)

(58) Field of Classification Search
CPC ..... G01N 21/956; G01N 21/88; G01N 21/47; G01N 21/00; G01B 9/00
USPC ...................................................... 356/237.5
See application file for complete search history.

(56) References Cited

U.S. PATENT DOCUMENTS

| 5,864,394 | A | * | 1/1999 | Jordan et al. ............... 356/237.2 |
| 6,341,042 | B1 | * | 1/2002 | Matsunaka et al. ........... 359/618 |
| 6,466,315 | B1 | * | 10/2002 | Karpol et al. ............... 356/237.4 |
| 7,426,023 | B2 | | 9/2008 | Ohshima et al. |
| 7,492,451 | B2 | * | 2/2009 | Vaez-Iravani et al. ..... 356/237.2 |

(Continued)

FOREIGN PATENT DOCUMENTS

JP 2000-260376 A 9/2000
JP 2010236966 A 10/2010

OTHER PUBLICATIONS

International Search Report and Written Opinion mailed on Feb. 26, 2014, for PCT Application No. PCT/US2013/071106 filed on Nov. 20, 2013, by KLA-Tencor Corporation, 9 pages.

*Primary Examiner* — Tarifur Chowdhury
*Assistant Examiner* — Isiaka Akanbi
(74) *Attorney, Agent, or Firm* — Spano Law Group; Joseph S. Spano (57) ABSTRACT

Methods and systems for reshaping the beam intensity distribution of an illumination light supplied to a specimen under inspection are presented. A scanning surface inspection system includes a beam shaping element that flattens the beam intensity distribution of a beam of light generated by an illumination source. The reshaped illumination light is directed to the wafer surface over an illumination spot. With a flattened beam intensity distribution, the incident beam power can be increased without the beam intensity exceeding the damage threshold of the wafer at any particular location. In addition, the illumination spot is shaped by the beam shaping element to have a variable beam width in a direction parallel to the inspection track. The location of a defect within an inspection area having a variable beam width is estimated based on an analysis of the output of the detector.

18 Claims, 6 Drawing Sheets

(56) References Cited

U.S. PATENT DOCUMENTS

| | | |
|---|---|---|
| 7,952,083 B2 | 5/2011 | Shichi et al. |
| 8,194,240 B1* | 6/2012 | Vaez-Iravani et al. ......... 356/124 |
| 2004/0076322 A1 | 4/2004 | Guetta |
| 2005/0170569 A1* | 8/2005 | Yazaki et al. .................. 438/155 |
| 2006/0256325 A1 | 11/2006 | Mcmillan et al. |
| 2008/0159112 A1 | 7/2008 | Van Der Lee et al. |
| 2009/0224180 A1 | 9/2009 | Aigner |
| 2009/0299655 A1* | 12/2009 | Biellak et al. .................... 702/40 |
| 2010/0274392 A1 | 10/2010 | Igari et al. |
| 2012/0229802 A1* | 9/2012 | Wolters et al. ............. 356/237.5 |
| 2012/0314211 A1 | 12/2012 | Ando et al. |
| 2013/0016346 A1 | 1/2013 | Romanovsky et al. |

* cited by examiner

INSPECTION BEAM SHAPING FOR IMPROVED DETECTION SENSITIVITY

CROSS REFERENCE TO RELATED APPLICATION

The present application for patent claims priority under 35 U.S.C. §119 from U.S. provisional patent application Ser. No. 61/728,707, entitled "Method of Shaping Inspection Beam with Improved Detection Sensitivity," filed Nov. 20, 2012, the subject matter of which is incorporated herein by reference.

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a scanning surface inspection system that illuminates and inspects an unpatterned wafer surface. The wafer is scanned under an illumination spot until the desired portion of the wafer surface is inspected. Typically, a laser based illumination source generates illumination light with a Gaussian beam intensity profile. In high-power, laser-based inspection systems, the power density of the incident laser beam is capable of damaging the wafer surface. For inspection systems employing a short-pulsed laser illumination source, substrate damage is primarily related to peak power density. An excessive amount of heat is generated by the interaction of the incident optical radiation with the wafer surface, particularly in areas of incidence subject to incident light with peak power density.

Typically, overall incident beam power is reduced by dumping a portion of the illumination light generated by the illumination source to avoid reaching the thermal damage threshold. In some examples, up to 85% of the beam power generated by the illumination source is dumped to avoid damaging the wafer. In typical bare wafer applications that are shot noise limited, the loss of overall beam power results in a loss of defect detection sensitivity.

Improvements to scanning surface inspection systems are desired to detect defects in the inspection path of an illumination spot on a wafer surface with greater sensitivity while avoiding thermal damage to the wafer surface.

SUMMARY

Methods and systems for reshaping the beam intensity distribution of an illumination light supplied to a specimen under inspection are presented.

In one aspect, a scanning surface inspection system includes a beam shaping element that receives a beam of light generated by an illumination source and reshapes the beam intensity distribution of the illumination light. The reshaped beam of illumination light has a flattened beam intensity distribution. This reshaped illumination light is directed to the wafer surface over an illumination spot. In this manner, incident beam power is increased without the beam intensity exceeding the damage threshold of the wafer at any particular location. Thus, defect sensitivity is increased while thermal damage to the wafer is avoided.

In some embodiments, the beam intensity distribution of the illumination light is reshaped to have a beam intensity distribution with a variance of less than 25% from an average intensity value across a width of an inspection track illuminated by the reshaped illumination light. In some other embodiments, the beam intensity distribution of the illumination light is reshaped have a beam intensity distribution with a variance of less than 10% from an average intensity value across a width of an inspection track illuminated by the reshaped illumination light.

In another aspect, the illumination spot is shaped by a beam shaping element to have a variable beam width in a direction parallel to the inspection track. For example, in a spiral scanning system, such as the system illustrated in FIGS. 1 and 2, the direction parallel to the inspection track is the tangential direction.

Figure 2:
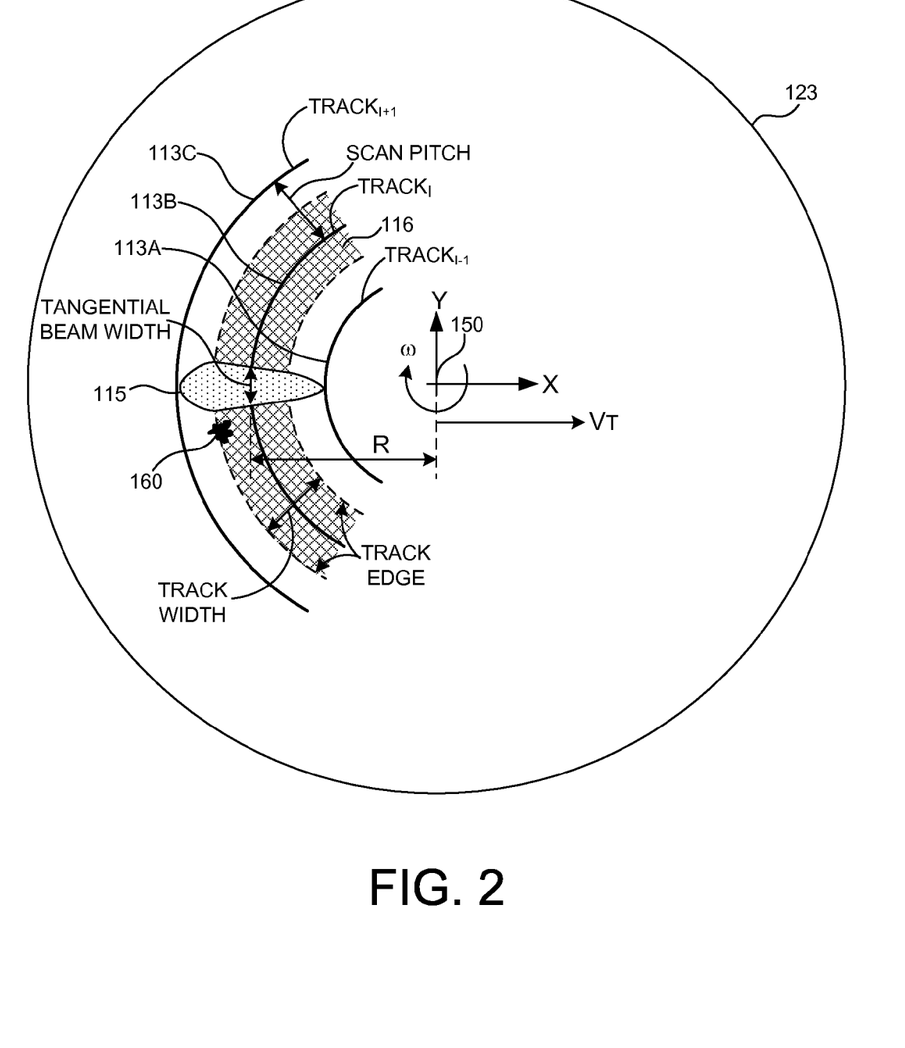
FIG. 2 is a simplified diagram illustrative of a wafer 123 illuminated by a reshaped illumination beam over an illumination spot 115.

In yet another aspect, the location of a defect illuminated by an illumination spot having a beam width that varies across the inspection track is estimated based on an analysis of the output of the detector. As illustrated in FIG. 2, illumination spot 115 has a tangential beam width that varies linearly across the inspection track. Because the tangential beam width varies linearly across the inspection track, the time a defect spends within illumination spot 115 varies depending on its location within the inspection track. The amount of time a defect spends within illumination spot 115 is measured by the duration of its contribution to the output signal generated a detector. For example, a measure of time that a defect spends within illumination spot 115 may be determined based on the duration of time that the output signal exceeds a threshold value. The location of the defect within the inspection track is determined from the duration of time and the known variation of the beam width across the inspection track.

In yet another aspect, inspection system 100 is configured to selectively include or remove any of a number of beam reshaping elements from the beam path between an illumination source and the wafer. In this manner, an appropriate beam shaping element, or set of beam shaping elements may be selectively employed for inspection modes where excess laser power is available, and not employed for inspection modes where full laser power is used without inducing thermal damage (e.g., low sensitivity, high throughput modes).

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
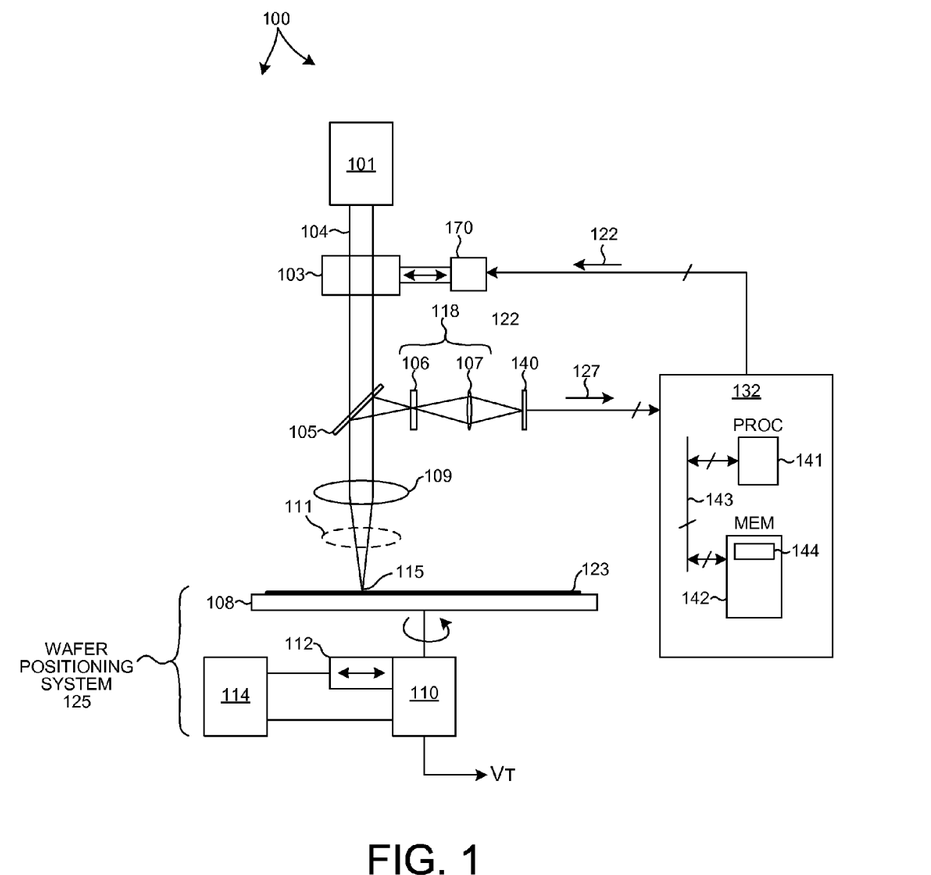
FIG. 1 is a simplified diagram illustrative of one embodiment of an inspection system including a beam shaping element 103 configured to reshape the beam intensity distribution of illumination light supplied to a specimen under inspection.

FIG. 1 is a simplified schematic view of one embodiment of a surface scanning inspection system 100 that may be used to perform the inspection methods described herein. For simplification, some optical components of the system have been omitted. By way of example, folding mirrors, polarizers, beam forming optics, additional light sources, additional collectors, and additional detectors may also be included. All such variations are within the scope of the invention described herein. The inspection system described herein may be used for inspecting patterned, as well as unpatterned wafers.

As illustrated in FIG. 1, a wafer 123 is illuminated by a normal incidence beam 111 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

In one aspect, system 100 includes a beam shaping element 103 that reshapes the beam intensity distribution of illumination light 104 to generate a reshaped beam of illumination light 111 with a flattened beam intensity distribution. This "reshaped illumination light" is directed to the wafer surface and is incident to the surface of wafer 123 over an illumination spot 115. In one embodiment, beam shaping element 103 includes a diffractive optical element to generate the desired intensity profile. In other embodiments, beam shaping element 103 includes an optical beam shaper to generate the desired intensity profile. In other embodiments, beam shaping element 103 includes an apodizer to generate the desired intensity profile. However, due to the attenuation of illumination power associated with apodizers, it is preferable to limit the use of apodizers to inspection modes that are not starved for illumination power. A beam splitter 105 directs the reshaped illumination light to an objective lens 109. Objective lens 109 focuses the reshaped illumination light 111 onto a wafer 123 at illumination spot 115. In this manner, illumination spot 115 is shaped and sized by the projection of light emitted from beam shaping element 103 onto the surface of wafer 123. As illustrated in FIG. 2, illumination spot 115 is located a distance, R, from the geometric center of wafer 123.

In some embodiments, reflected/scattered light is collected and detected from all of the area of illumination spot 115 over a particular sample period by inspection system 100. In this manner, as much light as possible is collected by inspection system 100. However, in some other embodiments, reflected/scattered light is collected and detected from a portion of the area of illumination spot 115 over a particular sample period by inspection system 100. System 100 includes collection optics 118 to collect light scattered and/or reflected by wafer 123 during the scan and to focus the collected light onto detector 140. An output signal 127 generated by detector 140 is supplied to a computer 132 for signal processing to determine the presence of anomalies and their characteristics.

Collection optics 118 may include a lens, a compound lens, or any appropriate lens known in the art. Alternatively, any element of collection optics 118 may be a reflective or partially reflective optical component, such as a mirror. In addition, although particular collection angles are illustrated in FIG. 1, it is to be understood that the collection optics may be arranged at any appropriate collection angle. The collection angle may vary depending upon, for example, the angle of incidence and/or topographical characteristics of the specimen.

Detector 140 generally functions to convert the scattered light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen. The term "single detector" is used herein to describe a detector having only one sensing area, or possibly several sensing areas (e.g., a detector array or multi-anode PMT). Regardless of number, the sensing areas of a single detector are embodied within a single enclosure. In the depicted embodiment, a "single detector" is associated with a particular illumination spot (e.g., detector 140 is a detector employed to generate an output signal associated with an inspection area illuminated by illumination spot 115). However, in other embodiments, additional "single detectors" may be employed to each generate an output signal associated with an illumination spot. For example, multiple "single detectors" may be employed to detect light collected from an inspection area illuminated by illumination spot 115, each at different collection angles.

In some embodiments of a scanning surface inspection system, a single detector is employed to detect light collected from a particular inspection area illuminated by an illumination spot. In the context of a surface scanning inspection system, such as system 100, detector 140 generates a single output signal 127 indicative of the light collected from an inspection area illuminated by illumination spot 115. A single output signal allows for efficient detection of defects with high throughput. In other words, in these embodiments, imaging detectors (i.e., a detector(s) that generates a number of separate output signals indicative of light collected over different inspection areas illuminated by illumination spot 115) are not employed due to their impact on throughput. However, the use of imaging detectors for other characterization tasks may be contemplated. In this manner, computationally burdensome data collection and processing associated with imaging is avoided, and satisfactory throughput rates can be achieved. Although, in these embodiments, imaging detectors are not employed, an image of a scanned area can be obtained by re-arranging the outputs from detector 140, which have been stored in a memory 142 of a computer 132.

System 100 also includes various electronic components (not shown) needed for processing the scattered signals detected by detector 140. For example, system 100 may include amplifier circuitry to receive output signal 127 from detector 140 and to amplify the output signal by a predetermined amount. In addition, an analog-to-digital converter (ADC) (not shown) is included to convert the amplified signals into a digital format suitable for use within processor 141. In one embodiment, the processor may be coupled directly to an ADC by a transmission medium. Alternatively, the processor may receive signals from other electronic components coupled to the ADC. In this manner, the processor may be indirectly coupled to the ADC by a transmission medium and any intervening electronic components.

In general, processor 141 is configured to detect features, defects, or light scattering properties of the wafer using electrical signals obtained from each detector. The signals produced by the detector are representative of the light detected by a single detector (e.g., detector 140). The processor may include any appropriate processor known in the art. In addition, the processor may be configured to use any appropriate defect detection algorithm or method known in the art. For example, the processor may use a die-to-database comparison or a thresholding algorithm to detect defects on the specimen.

In addition, inspection system 100 may include peripheral devices useful to accept inputs from an operator (e.g., keyboard, mouse, touchscreen, etc.) and display outputs to the operator (e.g., display monitor). Input commands from an operator may be used by processor 141 to adjust threshold values used to control illumination power. The resulting power levels may be graphically presented to an operator on a display monitor.

System 100 can use various imaging modes, such as bright field, dark field, and confocal. For example, in the embodiment depicted in FIG. 1, detector 140 generates a bright field signal. As illustrated in FIG. 1, some amount of light scattered from the surface of wafer 123 at a narrow angle is collected by objective lens 109. This light passes back through objective lens 109 and impinges on beam splitter 105. Beam splitter 105 transmits a portion of the light to collection optics 118, which in turn focuses the light onto detector 140. In this manner a bright field signal is generated by detector 140. Collection optics 118 includes imaging lens 107 that images the reflected light collected by objective lens 109 onto detector array 140. An aperture or Fourier filter 106, which can rotate in synchronism with the wafer, is placed at the back focal plane of objective lens 109. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example (not shown), a detector generates dark field images by imaging scattered light collected at larger field angles. In another example, a pinhole that matches the incident spot 115 can be placed in front of a detector (e.g., detector 140) to generate a confocal image. U.S. Pat. No. 6,208,411, which is incorporated by reference herein, describes these imaging modes in further detail. In addition, various aspects of surface inspection system 100 are described in U.S. Pat. No. 6,271,916 and U.S. Pat. No. 6,201,601, both of which are incorporated herein by reference.

In the embodiment illustrated in FIG. 1, wafer positioning system 125 moves wafer 123 under a stationary beam of illumination light 111. Wafer positioning system 125 includes a wafer chuck 108, motion controller 114, a rotation stage 110 and a translation stage 112. Wafer 123 is supported on wafer chuck 108. As illustrated in FIG. 2, wafer 123 is located with its geometric center 150 approximately aligned with the axis of rotation of rotation stage 110. In this manner, rotation stage 110 spins wafer 123 about its geometric center at a specified angular velocity, $\omega$, within an acceptable tolerance. In addition, translation stage 112 translates the wafer 123 in a direction approximately perpendicular to the axis of rotation of rotation stage 110 at a specified velocity, $V_T$. Motion controller 114 coordinates the spinning of wafer 123 by rotation stage 110 and the translation of wafer 123 by translation stage 112 to achieve the desired scanning motion of wafer 123 within scanning surface inspection system 100.

In some embodiments, system 100 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

In an exemplary operational scenario, inspection begins with an inspection area illuminated by illumination spot 115 located at the geometric center 150 of wafer 123 and then wafer 123 is rotated and translated until the inspection area illuminated by illumination spot 115 reaches the outer perimeter of wafer 123 (i.e., when R equals the radius of wafer 123). Due to the coordinated motion of rotation stage 110 and translation stage 112, the inspection area illuminated by illumination spot 115 traces a spiral path on the surface of wafer 123. The spiral path of the inspection area illuminated by illumination spot 115 on the surface of wafer 123 is referred to as an inspection track. A portion of an inspection track 116 is illustrated as a cross-hatched area in FIG. 2. Hence, the inspection area for the moment in time illustrated in FIG. 2 is the intersection of inspection track 116 and illumination spot 115. For purposes of illustration, a locus of points centered within the inspection track 116 traces a spiral path 113 on the surface of wafer 123. Portions 113a, 113b, and 113c of an exemplary spiral path 113 of inspection track 116 are illustrated in FIG. 2 as $TRACK_{i-1}$, $TRACK_i$, and $TRACK_{i+1}$, respectively. The inspection track 116 has a track width, $W_{TRACK}$, spanning across the inspection track from one track edge to the other. The distance between adjacent portions of an inspection track (e.g., distance between $TRACK_{i+1}$ and $TRACK_1$) is referred to as the scan pitch of the scanning surface inspection system 100. Ideally, the track edge of a portion of an inspection track abuts the track edge of an adjacent inspection track. In this manner, the surface of the wafer is covered by the inspection track. However, in practice, the width of the inspection track is selected to be slightly larger than the scan pitch to assure there is no gap between adjacent tracks. This margin accounts for positioning jitter in a practical inspection system. In some embodiments, the width of inspection track 116 is approximately twice the scan pitch. In this manner, a particular location on the wafer surface is sampled at least twice by adjacent instances of inspection track 116.

As illustrated in FIG. 2, illumination spot 115 is centered on the inspection track 116. Illumination spot 115 is typically sized to span a distance that is larger than the track width (e.g., two to three times the inspection track width) in a direction perpendicular to the inspection track. In a spiral scanning system, such as the system illustrated in FIGS. 1 and 2, the direction perpendicular to the inspection track is the radial direction. As illustrated in FIG. 2, the radial beam width of illumination spot 115 is approximately twice the inspection track width. However, in some embodiments, illumination spot 115 may be sized to span a distance that is approximately the size of the inspection area.

In one aspect, illumination spot 115 is shaped by beam shaping element 103 to have a variable beam width in a direction parallel to the inspection track 116. In a spiral scanning system, such as the system illustrated in FIGS. 1 and 2, the direction parallel to the inspection track is the tangential direction. Hence, the tangential beam width of illumination spot 115 varies across the inspection track 116.

Figure 3:
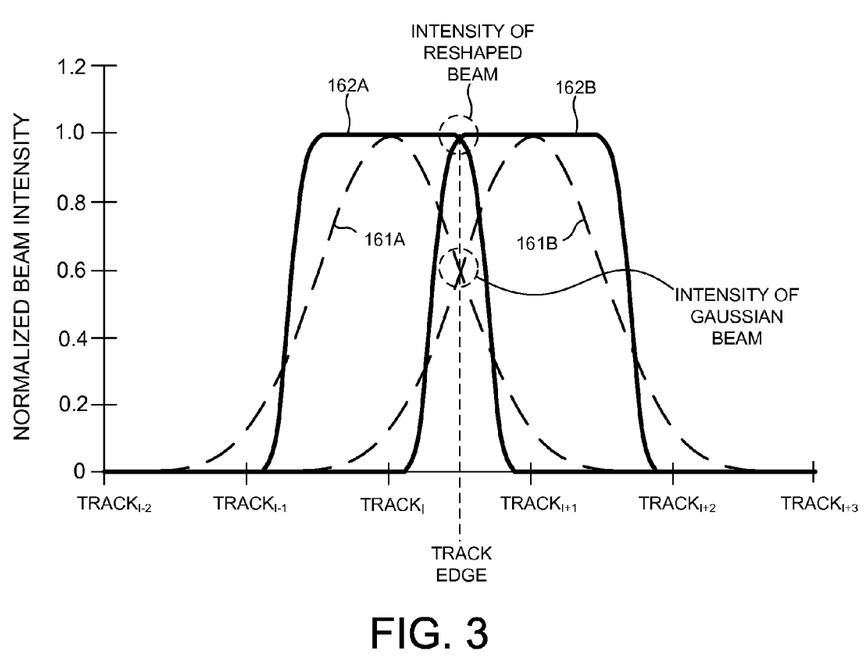
FIG. 3 is a plot illustrative of both Gaussian beam intensity distributions and flattened beam intensity distributions centered over adjacent inspection tracks.

As discussed hereinbefore, a laser based illumination source typically generates illumination light with a peaked beam intensity profile. In many examples, the peaked beam intensity profile is Gaussian, or approximately Gaussian. In some inspection modes (e.g., inspection modes where sensitivity is emphasized at the cost of throughput), the peak intensity of the incident laser beam (i.e., the intensity near the center of the beam where the Gaussian beam intensity profile is maximal) is capable of damaging the wafer surface. Typically, overall incident beam power is reduced by dumping a portion of the illumination light to avoid reaching the thermal damage threshold. For example, the beam intensity distribution across illumination spot 115 in the radial direction is illustrated in FIG. 3. The typical case of a normalized Gaussian beam intensity distribution across illumination spot 115 centered over $TRACK_i$ is illustrated as beam intensity distribution 161A. The same normalized Gaussian beam intensity distribution centered over track $TRACK_{i+1}$ is illustrated as beam intensity distribution 161B. As illustrated, the incident beam power has been attenuated such that the beam intensity remains below the damage threshold of the wafer. However, the illumination intensity of the Gaussian beam at the track edge is significantly lower than the illumination intensity at the center of the track. This results in a reduced sensitivity to defects located near the track edge (e.g., particle 160 illustrated in FIG. 2).

In another aspect, inspection system 100 reshapes the beam intensity distribution of the illumination light to generate an illumination light with a flattened beam intensity distribution. In this manner, incident beam power is increased without the beam intensity exceeding the damage threshold of the wafer at any particular location. Thus, defect sensitivity is increased while thermal damage to the wafer is avoided.

In some embodiments, the beam intensity distribution of illumination light 104 is reshaped by reshaping element 103 to generate a reshaped illumination light 111 with a beam intensity distribution with a variance of less than 25% from an average intensity value across a width of an inspection track illuminated by the reshaped illumination light.

In some other embodiments, the beam intensity distribution of illumination light 104 is reshaped by reshaping element 103 to generate a reshaped illumination light 111 with a beam intensity distribution with a variance of less than 10% from an average intensity value across a width of an inspection track illuminated by the reshaped illumination light.

In some examples, the beam intensity distribution of reshaped illumination light 111 is uniform across the track width. For example, the beam intensity distribution across illumination spot 115 in the radial direction is illustrated in FIG. 3. A uniform beam intensity distribution across illumination spot 115 over the track width centered over $TRACK_i$ is illustrated as beam intensity distribution 162A. The same uniform beam intensity distribution centered over $TRACK_{i+1}$ is illustrated as beam intensity distribution 162B. As illustrated, the incident beam intensity is uniformly high across the inspection track, rather than dropping off from the center of the track to the track edge as is the case for peaked beam intensity distributions 161A and 161B. By way of example, peaked beam intensity distributions 161A and 161B are Gaussian. Thus, beam power across the inspection track is significantly greater. This is achieved without the beam intensity exceeding the damage threshold of the wafer at any particular location.

For the case of a uniform beam intensity distribution across the track width, the illumination intensity is raised relative to a Gaussian beam intensity distribution at the track edge by a factor of approximately 1.6. Hence, for an inspection scenario that imposes limits on beam intensity to avoid thermal damage to the wafer, the maximum SNR for a flattened beam intensity distribution is approximately 57% higher than the maximum SNR for a Gaussian beam intensity distribution. This increase in achievable SNR corresponds to sensitivity to defects that are approximately 8% smaller.

In some examples, the position of a defect may be determined with sub-track accuracy by fitting the detected intensity of two adjacent tracks to the measured beam shape at the plane of incidence to wafer 123. As illustrated in FIG. 3, by way of example, an illumination light having a Gaussian beam intensity distribution has a varying beam intensity distribution across an inspection track, thus enabling a successful fitting. However, by employing a uniform beam intensity distribution across the inspection track, information about the location of a particle is diluted because the defect signals associated with successive scans of the particle location (e.g., each location is scanned at least twice) is independent of the particle location between inspection tracks. To retain the ability to estimate defect locations with sub-track accuracy with improved defect sensitivity, beam shaping element 103 is configured to generate reshaped illumination light with a beam width, measured in a direction parallel to the trajectory of the inspection track, which varies across the inspection track.

Figure 4:
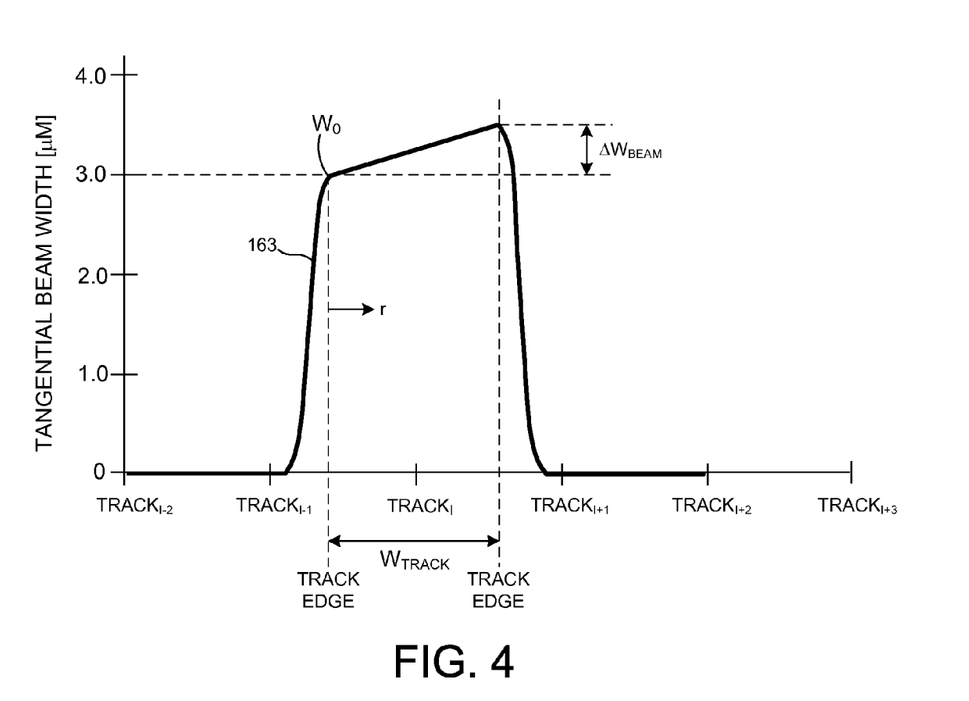
FIG. 4 is a plot illustrative of the tangential beam width of the reshaped illumination beam over illumination spot 115.

In some embodiments, illumination light 104 is reshaped by reshaping element 103 to generate a reshaped illumination light 111 such that a tangential beam width of illumination spot 115 varies linearly in the radial direction across the inspection track 116. FIG. 2 illustrates an illumination spot 115 having a tangential beam width that varies linearly across the inspection track 116. FIG. 4 illustrates the tangential beam width 163 of an exemplary illumination spot 115 centered over TRACK$_i$. As illustrated, the tangential beam width is increased by an amount, $\Delta W_{BEAM}$, across TRACK$_i$.

Figure 5:
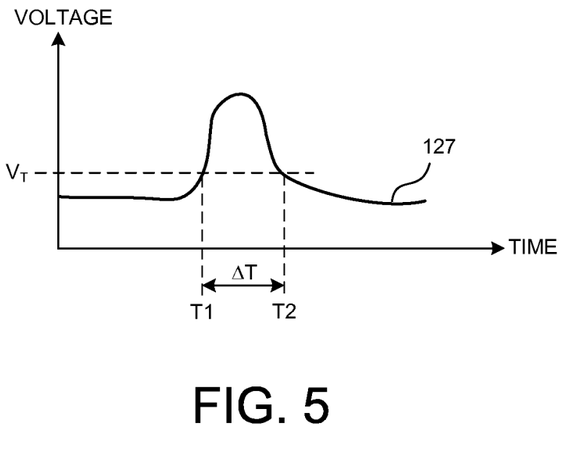
FIG. 5 is a plot illustrative of an exemplary output signal 127.

In yet another aspect, the location of a particle within an inspection area illuminated by an illumination spot having a beam width that varies across the inspection track is estimated based on an analysis of the output of the detector. As illustrated in FIG. 2, illumination spot 115 has a tangential beam width that varies linearly across the inspection track 116. Because the tangential beam width varies linearly across the inspection track, the time a defect (e.g. particle 160) spends within the inspection area illuminated by illumination spot 115 varies depending on its location within the inspection track. In other words, the defect travels at a constant velocity under illumination spot 115 regardless of its position within the inspection track (assuming the inspection track width is a much smaller value than the radial position of the inspection track on wafer 123). Hence, the greater the tangential beam width at a particular location, the longer the period of time the particle will spend within the inspection area illuminated by illumination spot 115. For example, as illustrated in FIG. 2, particle 160 located within TRACK$_i$ would spend more time within the inspection area illuminated by illumination spot 115 if it was located near the track edge furthest away from the center of wafer 123 than if it was located near the track edge nearest the center of wafer 150. The amount of time particle 160 spends within the inspection area within illumination spot 115 is measured by the duration of its contribution to output signal 127 generated by detector 140. FIG. 5 illustrates an exemplary time trace of output signal 127. When particle 160 passes within the inspection area illuminated by illumination spot 115, the amplitude of output signal 127 increases, and then decreases as particle 160 passes through the inspection area illuminated by illumination spot 115. A measure of time that particle 160 spends within the inspection area illuminated by illumination spot 115 may be determined based on a time, $\Delta T$, that output signal 127 exceeds a threshold value, $V_T$. The location of particle 150 within TRACK$_i$ can be calculated from the measured time $\Delta T$. For example, the distance, W, traversed by particle 160 within the inspection area illuminated by illumination spot 115 can be estimated based on the measured time, $\Delta T$, using equation (1).

$$W = \omega R (\Delta T) \quad (1)$$

Since the tangential beam width of illumination spot 115 varies linearly as a function of radial location, the location, r, within the inspection area illuminated by illumination spot 115 may be determined based on the distance, W, using equation (2), $$r = \frac{W_{track}}{\Delta W_{beam}} (W - W_0) \quad (2)$$

where $W_{TRACK}$ is the track width, $\Delta W_{BEAM}$ is the change in tangential beam width across the inspection track, and $W_0$ is the tangential beam width at the track edge of TRACK$_i$ closest to the center of wafer 123. For example, as illustrated by FIGS. 2 and 4, the tangential beam width of illumination spot 115 varies from three micrometers at the track edge closest to the center of the wafer to 3.3 micrometers at the track edge furthest from the center of the wafer. Moreover, the tangential beam width varies linearly from 3 micrometers to 3.3 micrometers across TRACK$_i$. In this manner, the location of particle 160 within the inspection track can be estimated.

Although, as illustrated in FIG. 4, the tangential beam width of reshaped illumination light incident to wafer 123 over illumination spot 115 varies linearly across inspection track 116, many other variations may be contemplated. In general, the tangential beam width could vary across the inspection track in accordance with any single valued function. In this manner, a single location within the inspection track can be identified as the location of a defect based on analysis of the output signal generated by the detector.

Although, as illustrated in FIG. 5, a single valued threshold, $V_T$, is employed to estimate the time period that a defect remains within an inspection area illuminated by an illumination spot, any suitable threshold value may be contemplated. For example, the threshold value may vary based on noise levels present in the measurement. A set of threshold values may be employed. For example a first threshold value could be used to identify when a defect has entered an inspection area illuminated by an illumination spot, and another, different threshold value may be used to identify when the defect has exited the inspection area illuminated by the illumination spot.

In yet another aspect, inspection system 100 is configured to selectively include or remove any of a number of beam reshaping elements (e.g., beam shaping element 103) from the beam path between illumination source 101 and wafer 123. In this manner, an appropriate beam shaping element, or set of beam shaping elements may be selectively employed for inspection modes where excess laser power is available, and not employed for inspection modes where full laser power is used without inducing thermal damage (e.g., low sensitivity, high throughput modes). For example, as illustrated in FIG. 1, inspection system 100 includes an actuator 170 configured to selectively move beam shaping element 103 into and out of the beam path between illumination source 101 and wafer 123 in response to a command signal 122 generated by computer 132. In some examples, actuator 170 is an actuator (e.g., linear or rotary actuator) that physically moves beam shaping element 103 in and out of the beam path. In another example, actuator 170 includes one or more beam deflection elements (e.g., galvo mirrors, etc.) that selectively direct the beam path through or around beam shaping element 103.

Inspection system 100 includes a processor 141 and an amount of computer readable memory 142. Processor 141 and memory 142 may communicate over bus 143. Memory 142 includes an amount of memory 144 that stores a program code that, when executed by processor 141, causes processor 141 to determine the desired inspection mode and generate a control signal that causes the appropriate beam shaping element(s) to be selectively included or removed from the illumination beam path based on the desired inspection mode.

In the depicted embodiments, computer 132 includes processor 141 and memory 142 and controls whether one or more beam shaping elements are included in the illumination beam path in accordance with the methods and systems described herein. Hence, in some embodiments, computer 132 controls whether beam shaping occurs and the nature of the beam shaping as described herein. However, in other embodiments, this control functionality may be implemented by any other general purpose computer or dedicated hardware of inspection system 100 configured to operate in an analogous manner.

Although, reshaping of the beam intensity distribution of the illumination light has been described hereinbefore with reference to an individual illumination spot (e.g., illumination spot 115), the methods and systems described herein may also be applied analogously to a multi-spot surface inspection system. In a multi-spot inspection system, a number of illumination spots are employed simultaneously. Illumination light is supplied to these illumination spots from one or more illumination sources. Beam shaping elements, such as beam shaping element 103 described herein, may be selectively placed in the beam path between any of the one or more illumination sources and any of the multiple illumination spots to reshape the beam intensity distribution of the illumination light incident to the illumination spots as described herein. In this manner, defect sensitivity at any of the illumination spots may be improved. Typically, illumination spots are configured with considerable spacing between spots such that inspection results may be interleaved among successive portions of an inspection track and cross-talk at the detectors is minimized. U.S. Pat. Publication No. 2009/0225399, which is incorporated by reference herein, describes multi-spot scanning techniques in further detail.

Figure 6:
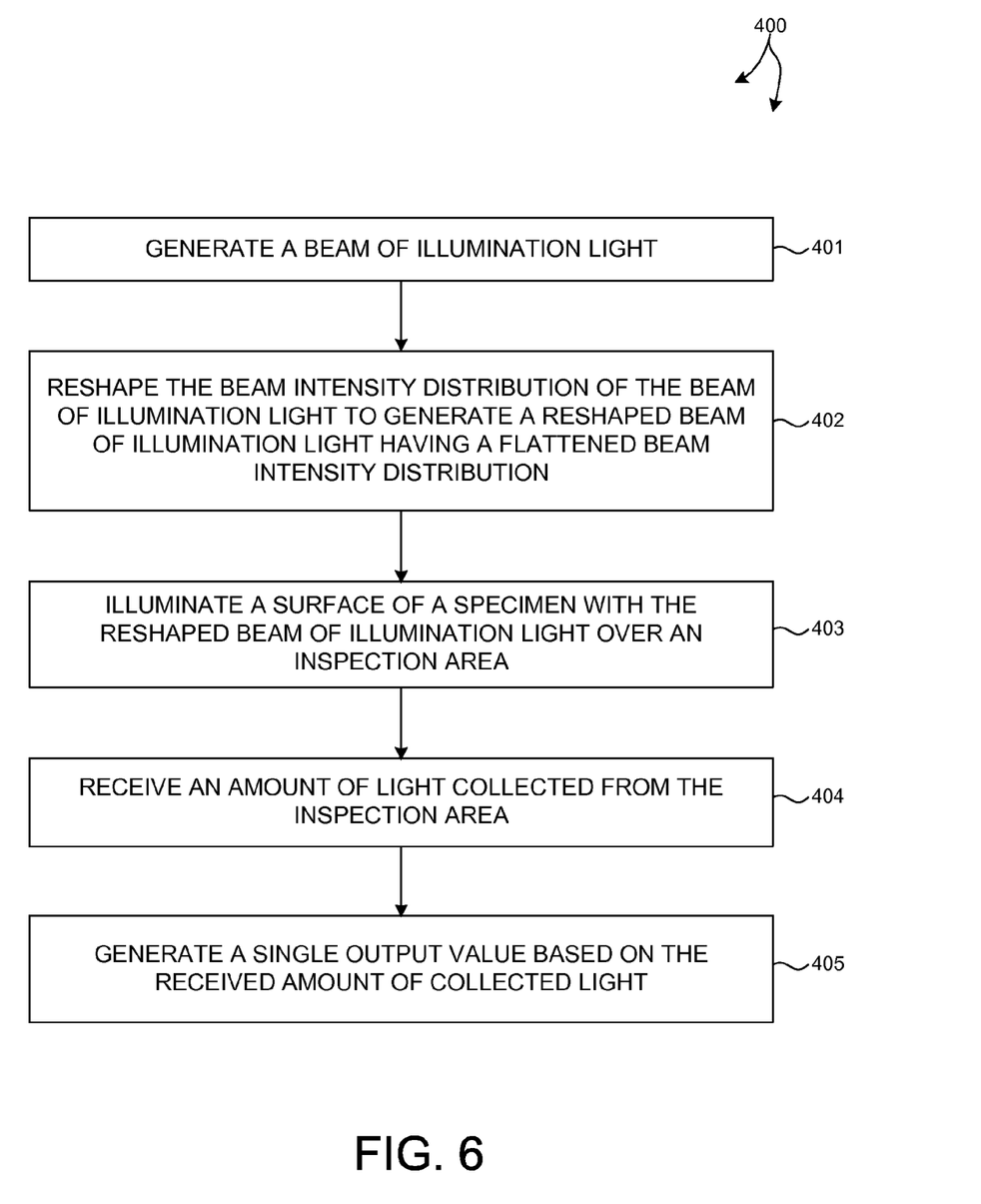
FIG. 6 is a flowchart illustrative of a method 400 of reshaping the beam intensity distribution of illumination light supplied to a specimen under inspection.

FIG. 6 illustrates a flowchart of an exemplary method 400 useful for reshaping the beam intensity distribution of illumination light incident on an illumination spot of a specimen to improve defect sensitivity without inducing thermal damage to a wafer surface. In one non-limiting example, inspection system 100, described with reference to FIG. 1 is configured to implement method 400. However, in general, the implementation of method 400 is not limited by the specific embodiments described herein.

In block 401, a beam of illumination light is generated by an illumination source.

In block 402, the beam intensity distribution of the illumination light is reshaped to generate a reshaped beam of illumination light having a flattened beam intensity distribution. In some examples, the reshaped illumination light has a beam intensity distribution with a variance of less than 25% from an average intensity value across a width of an inspection track illuminated by a portion of the reshaped beam of illumination light. In some examples, the reshaped illumination light has a beam intensity distribution with a variance of less than 10% from an average intensity value across a width of an inspection track illuminated by a portion of the reshaped beam of illumination light.

In block 403, a surface of a specimen is illuminated with the reshaped beam of illumination light over an inspection area illuminated by an illumination spot.

In block 404, an amount of light collected from the inspection area illuminated by the illumination spot is received, for example, by a detector.

In block 405, a single output value is generated based on the amount of collected light received by the detector.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, detector 140 can be replaced by a fiber array. In one example, inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, an inspection system may illuminate the wafer over more than one illumination area simultaneously. The multiple illumination areas may spatially overlap. The multiple illumination areas may be spatially distinct. In some embodiments, an inspection system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 123. In some embodiments an illumination area is made to scan in a repeated pattern along a scan line. The scan line may or may not align with the scan motion of wafer 123. Although as presented herein, wafer positioning system 125 generates motion of wafer 123 by coordinated rotational and translational movements, in yet another example, wafer positioning system 100 may generate motion of wafer 123 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, an inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction).

Accordingly, various modifications, adaptations, and combinations of various features of the described embodiments can be practiced without departing from the scope of the invention as set forth in the claims.

What is claimed is:

1. A method comprising:
   generating a beam of illumination light having a beam intensity distribution;
   reshaping the beam intensity distribution of the beam of illumination light to generate a reshaped beam of illumination light, the reshaped beam of illumination light having a beam intensity distribution with a variance of less than 25% from an average intensity value across a width of an inspection track illuminated by a portion of the reshaped beam of illumination light;
   illuminating a surface of a specimen with the reshaped beam of illumination light over an inspection area of the inspection track, wherein a beam width of the illumination light over the inspection area varies in a direction parallel to a trajectory of the inspection track as a single valued function of location across the inspection track;
   receiving an amount of light collected from the inspection area;
   generating an output signal based on the received amount of collected light;
   determining a duration of time the output signal exceeds a threshold value; and
   determining a location of a defect within the inspection track in a direction across the inspection track based on the duration of time.

2. The method of claim 1, wherein the beam intensity distribution of the beam of illumination light is approximately Gaussian.

3. The method of claim 1, further comprising:
   moving the specimen in a scanning motion such that the specimen tracks a spiral motion trajectory characterized by a scan pitch.

4. The method of claim 1, wherein the beam intensity distribution of the reshaped illumination light has a variance of less than 10% from the average intensity value across the width of the inspection track illuminated by the portion of the reshaped beam of illumination light.

5. The method of claim 1, wherein the beam width of the illumination spot in the direction parallel to the trajectory of the inspection track varies linearly across the inspection track from a first value to a second value.

6. The method of claim 1, wherein the reshaping involves passing the illumination light through any of a diffractive optical element, an optical beam shaper, and an apodizer.

7. The method of claim 1, wherein the receiving an amount of light scattered from the at least one illumination spot involves a single detector.

8. An inspection system comprising:
   an illumination source configured to generate a beam of illumination light;
   a beam shaping element that receives the beam of illumination light and generates a reshaped beam of illumination light having a beam intensity distribution with a variance of less than 25% from an average intensity value across a width of an inspection track illuminated by a portion of the reshaped beam of illumination light;
   an objective that focuses a first portion of the reshaped beam of illumination light to a first inspection area of the inspection track, wherein a beam width of the first portion of the reshaped beam of illumination light varies in a direction parallel to a trajectory of the inspection track as a single valued function of location across the inspection track;
   a first detector operable to receive a first amount of light collected from the first inspection area and generate an output signal based on the received amount of collected light; and
   a computing system configured to:
     determine a duration of time the output signal exceeds a threshold value; and
     determine a location of the defect within the inspection track in a direction across the inspection track based on the duration of time.

9. The inspection system of claim 8, further comprising:
   a wafer positioning system operable to move the wafer in a scanning motion such that the first inspection area moves across the surface of the wafer along an inspection path characterized by a scan pitch.

10. The inspection system of claim 8, wherein the beam of illumination light has a beam intensity distribution that is approximately Gaussian.

11. The inspection system of claim 8, wherein the beam intensity distribution of the reshaped illumination light has a variance of less than 10% from the average intensity value across the width of the inspection track illuminated by the portion of the reshaped beam of illumination light.

12. The inspection system of claim 8, wherein the beam width of the reshaped beam of illumination light in the direction parallel to the trajectory of the inspection track varies linearly across the inspection track from a first value to a second value.

13. The inspection system of claim 8, wherein the beam shaping element is any of a diffractive optical element, an optical beam shaper, and an apodizer.

14. The inspection system of claim 8, further comprising:
   a second detector operable to receive a second amount of light collected from a second inspection area illuminated by a second portion of the reshaped beam of illumination light incident on a second portion of the surface of the wafer, wherein the second detector generates an output signal based on the second amount of collected light, and wherein the objective focuses the second portion of the reshaped beam of illumination light onto the second inspection area.

15. An inspection system comprising:

an illumination source configured to generate a beam of illumination light having a peaked beam intensity distribution;

a beam shaping element that receives the beam of illumination light and generates a reshaped beam of illumination light having a flattened beam intensity distribution;

an objective that focuses a first portion of the reshaped beam of illumination light to an inspection area on a wafer surface, wherein a beam width of the first portion of the reshaped beam of illumination light varies in a direction parallel to a trajectory of the inspection track as a single valued function of location across the inspection track;

a single detector operable to receive a first amount of light collected from the inspection area and generate an output signal based on the received amount of collected light; and a computing system configured to:
  determine a duration of time the output signal exceeds a threshold value; and
  determine a location of the defect within the inspection track in a direction across the inspection track based on the duration of time.

16. The inspection system of claim 15, further comprising:
a wafer positioning system operable to move the wafer in a scanning motion such that the inspection area moves across the surface of the wafer along an inspection path characterized by a scan pitch.

17. The inspection system of claim 15, wherein the peaked beam intensity distribution of the beam of illumination light is approximately Gaussian.

18. The inspection system of claim 15, wherein the beam intensity distribution of the reshaped illumination light has a variance of less than 10% from an average intensity value across a width of an inspection track illuminated by a portion of the reshaped beam of illumination light.

* * * * *